(12) United States Patent
Brekke et al.

(10) Patent No.: US 7,261,695 B2
(45) Date of Patent: Aug. 28, 2007

(54) TRIGGER EXTRACTION FROM ULTRASOUND DOPPLER SIGNALS

(75) Inventors: Svein Brekke, Askøy (NO); Hans Garmann Torp, Trondheim (NO)

(73) Assignee: General Electric Company, Schenectady, NY (US)

( * ) Notice: Subject to any disclaimer, the term of this patent is extended or adjusted under 35 U.S.C. 154(b) by 360 days.

(21) Appl. No.: 10/796,834

(22) Filed: Mar. 9, 2004

(65) Prior Publication Data
US 2005/0203393 A1 Sep. 15, 2005

(51) Int. Cl.
*A61B 8/00* (2006.01)
(52) U.S. Cl. .................................... 600/443
(58) Field of Classification Search .............. 600/407, 600/409, 437, 443, 447, 509, 513, 521
See application file for complete search history.

(56) References Cited

U.S. PATENT DOCUMENTS

| | | | | |
|---|---|---|---|---|
| 3,813,654 A | * | 5/1974 | Clifton et al. | 600/453 |
| 5,513,640 A | * | 5/1996 | Yamazaki et al. | 600/455 |
| 5,704,361 A | * | 1/1998 | Seward et al. | 600/459 |
| 5,785,654 A | * | 7/1998 | Iinuma et al. | 600/441 |
| 6,014,473 A | * | 1/2000 | Hossack et al. | 382/294 |
| 6,174,287 B1 | * | 1/2001 | Resnick et al. | 600/458 |
| 6,652,462 B2 | * | 11/2003 | Bjaerum et al. | 600/450 |
| 6,673,017 B1 | * | 1/2004 | Jackson | 600/437 |
| 6,849,048 B2 | * | 2/2005 | Omiya | 600/443 |
| 6,980,844 B2 | * | 12/2005 | Schoisswohl | 600/407 |
| 2005/0033174 A1 | * | 2/2005 | Moehring et al. | 600/453 |

OTHER PUBLICATIONS

Dynamic 3D ultrasound imaging of the fetal heart, S. Brekke, E. Tegnander, H. Torp and S.H. Eik-Nes, IEEE Ultrasonic Symposium, Oct. 2002.

* cited by examiner

*Primary Examiner*—Francis J. Jaworski
(74) *Attorney, Agent, or Firm*—Small Patent Law Group; Dean D. Small

(57) ABSTRACT

A trigger extraction system for obtaining an event trigger for an event occurring in a region of interest includes a processor, a memory coupled to the processor, and a trigger extraction program stored in the memory for execution by the processor. The trigger extraction program includes instructions for accessing ultrasound trigger data from a trigger region intersecting a region of interest, analyzing the trigger data for a trigger characteristic, and storing an event trigger based on the trigger characteristic.

32 Claims, 4 Drawing Sheets

TRIGGER EXTRACTION FROM ULTRASOUND DOPPLER SIGNALS

BACKGROUND OF THE INVENTION

This invention relates generally to ultrasound imaging systems. In particular, this invention relates to identifying event triggers in ultrasound Doppler signals.

Some ultrasound imaging systems include the capability to present a looping series of ultrasound images. The looping series of images appears to the viewer as a short repeating movie or video of the internal structures imaged during a series of ultrasound firings. In a cardiology examination, for example, the imaging system may capture ultrasound images of the heart along with ECG data. The characteristics of the ECG signal are well known, and the imaging system may use those characteristics to synchronize the display of a loop of images of the heart, where each loop is generally an integer number of cardiac cycles.

In some cases, however, the ECG signal is not readily available. For example, ultrasound imaging of the fetal heart typically cannot rely of the fetal ECG signal. In part, this is because the operator cannot set ECG pads directly on the fetus. Although it is possible to place ECG pads on the mother to obtain the fetal ECG signal (a process called "fetal ECG"), this approach is not widely used because the signal from the fetus is very weak and is also disturbed by electrical pulses from the mother's body. Hence, the fetal ECG is not a feasible way of measuring fetal heart signals. The absence of the ECG signal general means that cumbersome manual methods must be used to input image synchronization information.

Note also that while the ECG signal may provide insight into how to temporally present a series of heart images, it is not generally indicative of other processes occurring in the body. Thus, even if the ECG signal is available, it may bear no relation to the structures that the imaging system needs to visualize for the operator.

Therefore, there is a need for extracting trigger information in ultrasound imaging systems that overcomes, at least in part, the difficulties set forth above and others previously experienced.

BRIEF DESCRIPTION OF THE INVENTION

In one embodiment, a trigger extraction system obtains event triggers for an event occurring in a region of interest. The trigger extraction system includes a processor, a memory coupled to the processor, and a trigger extraction program stored in the memory for execution by the processor. The trigger extraction program includes instructions for accessing ultrasound trigger data obtained from a trigger region, analyzing the trigger data for a trigger characteristic, and storing an event trigger based on the trigger characteristic.

In another embodiment, an ultrasound imaging system includes an ultrasound probe that obtains ultrasound trigger data from a trigger region, a processor, and a memory coupled to the processor. The memory stores a trigger extraction program as noted above. In addition, the memory stores an image display program that includes instructions for accessing the event trigger and for displaying at least one image in a sequence of images in synchronism with the event trigger. A display is included for showing the sequence of images.

BRIEF DESCRIPTION OF THE DRAWINGS

The components in the figures are not necessarily to scale, emphasis instead being placed upon illustrating the principles of the trigger extraction techniques. In the figures, like reference numerals designate corresponding parts throughout the different views.

DETAILED DESCRIPTION

Figure 1:
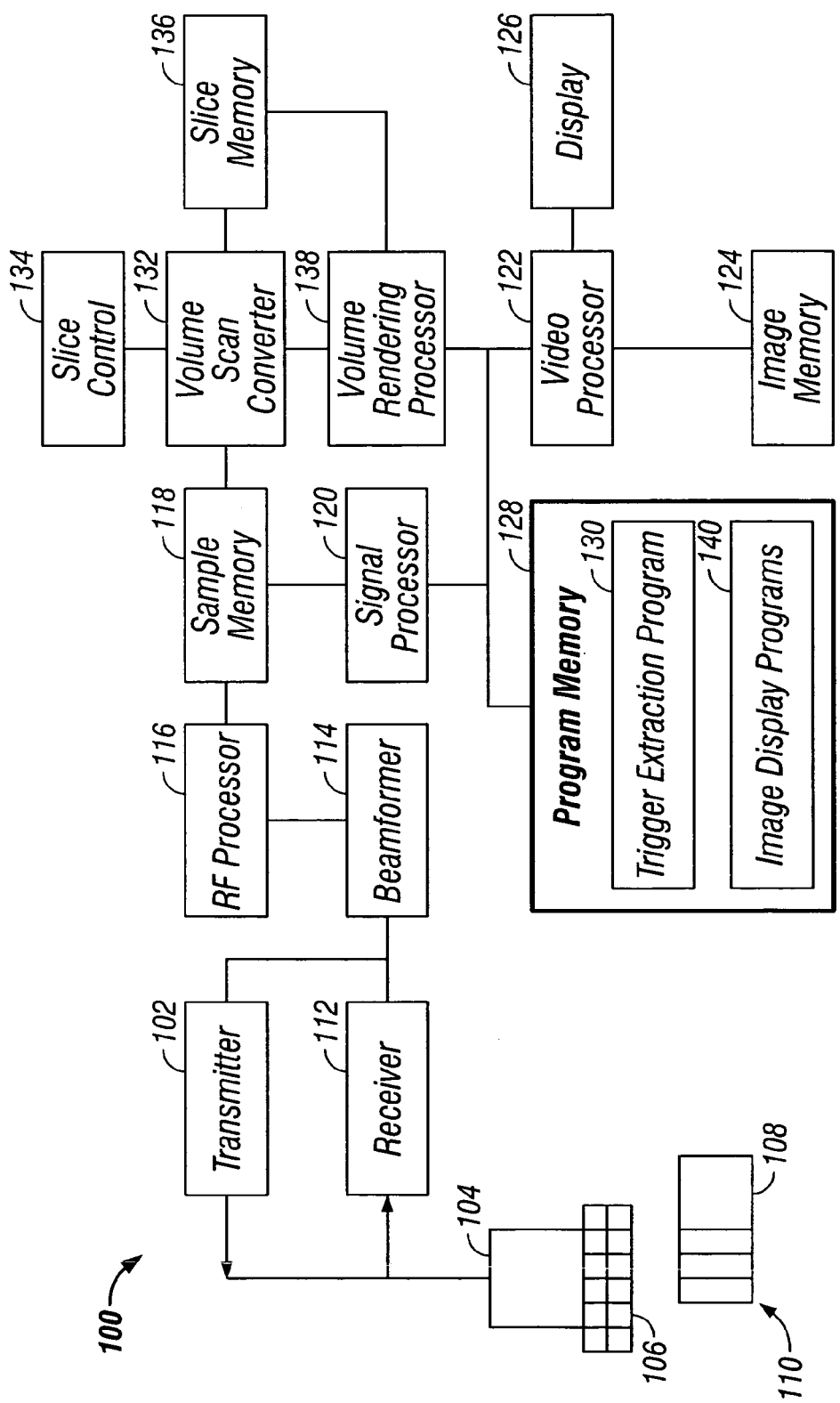
FIG. 1 illustrates an ultrasound imaging system.

Before turning in detail to the trigger extraction techniques, an exemplary ultrasound imaging system suitable for using the trigger extraction techniques is summarized with reference to FIG. 1. The trigger extraction techniques are not limited use with the system shown in FIG. 1, however. Rather, the techniques are generally applicable to a wide variety of medical imaging systems and image data.

FIG. 1 illustrates a diagram of the functional blocks of an ultrasound system 100 (or trigger extraction system). The functional blocks are not necessarily indicative of the division between hardware circuitry. Thus, for example, one or more of the functional blocks (e.g., processors or memories) may be implemented in a single piece of hardware (e.g., a general purpose signal processor or a block or random access memory, hard disk, or the like). Similarly, the programs may be stand alone programs, may be incorporated as subroutines in an operating system, may be functions in an installed imaging software package, and the like.

The ultrasound system 100 includes a transmitter 102 which drives an ultrasound probe 104. The ultrasound probe 104 includes multiple transducers 106 that emit pulsed ultrasonic signals into a region of interest 108 (e.g., a patient's chest). The probe 104 may be moved over the region of interest 108 in order to acquire image information in scan planes 110 of the region of interest 108.

The probe 104 may conform to one of many geometries, as examples, a 1D, 1.5D, 1.75D, or 2D probe. Structures in the region of interest 108 (e.g., a heart, blood cells, muscular tissue, and the like) back-scatter the ultrasonic signals. The resultant echoes return to the transducers 106.

In response, the transducers 106 generate electrical signals that the receiver 112 receives and forwards to the beamformer 114. The beamformer 114 processes the signals for steering, focusing, amplification, and the like. The RF signal passes through the RF processor 116 or a complex demodulator (not shown) that demodulates the RF signal to form in-phase and quadrature (I/Q) data pairs representative of the echo signals. The RF or I/Q signal data may then be routed directly to the sample memory 118 for temporary storage.

The ultrasound system 100 also includes a signal processor 120 to process the acquired ultrasound information (i.e., the RF signal data or IQ data pairs) and prepare frames of ultrasound information (e.g., graphical images) for display. To that end, the signal processor 120 may provide the ultrasound information to the video processor 122. The video processor 122 stores frame data in the image memory 124, and outputs the video signals that drive the display 126. The display 126 may be, as examples, a CRT or LCD monitor, hardcopy device, or the like.

The signal processor 120 executes instructions out of the program memory 128. The program memory 128 stores, for example, an operating system for the ultrasound system 100, image processing programs, and (as will be explained in detail below), a trigger extraction program 130. In general, the signal processor 120 information chosen from the configured ultrasound modalities present in the ultrasound imaging system 100. The signal processor 120 may process in real-time acquired ultrasound information during a scanning session as the echo signals are received. Additionally or alternatively, the ultrasound information may be stored temporarily in the sample memory 118 during a scanning session and processed in less than real-time in a live or off-line operation.

The ultrasound system 100 may acquire ultrasound information at a selected frame rate (e.g., 50 frames per second) and display those frames at the same or different frame rate on the display 126. The memories shown in FIG. 1 may store processed frames that are not scheduled for immediate display. For example, the image memory 124 may be sized to store several seconds or more of image frames. In one embodiment, as will be described in more detail below, the ultrasound system 100 stores the image frames with triggering information so that the ultrasound system 100 can present looping image sequences on the display 126, synchronized to selected events in the region of interest 108.

In addition or alternatively, the ultrasound system 100 may scan a volume from the region of interest 108. To that end, the probe 104 may be used in conjunction with techniques including 3D scanning, real-time 3D imaging, volume scanning, 2D scanning with transducers having positioning sensors, freehand scanning using a Voxel correlation technique, 2D or matrix array transducers and the like.

When the probe 104 moves, as examples, along a linear or arcuate path, it scans the region of interest 108. At each linear or arcuate position, the probe 104 obtains scan planes 110 from the region of interest 108. The scan planes 110 are collected to cover a selected thickness, for example, by collecting adjacent scan planes 110. The scan planes 110 are stored in the memory 118, and then passed to a volume scan converter 132. In some embodiments, the probe 104 may obtain lines instead of the scan planes 110, and the memory 118 may store lines obtained by the probe 104 rather than the scan planes 110.

The volume scan converter 132 receives a slice thickness setting from a control input 134, that an operator adjusts to choose the thickness of a slice to be created from the scan planes 110. The volume scan converter 132 creates a data slice from multiple adjacent scan planes 110. The number of adjacent scan planes 110 that form each data slice is dependent upon the thickness selected by the slice thickness control input 134. The data slice is stored in slice memory 136 for access by the volume rendering processor 138. The volume rendering processor 138, in conjunction with image display programs 140 in the program memory 128, performs volume rendering upon the data slice. The output of the volume rendering processor 138 passes to the video processor 122 and display 126.

In one mode of operation, the ultrasound system 100 displays sequences of images captured by the probe 104. One or more of the images may be displayed in synchronism with an event trigger determined by the trigger extraction program 130. As will be explained in more detail below, the trigger extraction program 130 accesses ultrasound image data stored in the memory 118, analyzes the image data for a trigger characteristic, and stores an event trigger based on the trigger characteristic.

As one example, the images may be images of a fetal heart. The trigger extraction program 130 may then determine event triggers based on fetal tissue movement at or near the heart. The event triggers may correspond, for example, to extremes of tissue movement speed.

Thus, the ultrasound system 100 may display a sequence of images (optionally looping) of the fetal heart to show the repetition of a heart cardiac cycle with selected frames displayed at times determined by the event triggers. An event trigger may be stored as a time stamp at which a certain event in the cyclic motion occurred. The events, for example, may correspond to atrial contraction, ventricular systole, ventricular diastole, and the like. More generally, a trigger event is an indicator obtained from ultrasound firings that temporally or spatially identifies an event, that occurs in the region of interest.

The image sequences are not limited to fetal hearts, however. Instead, the ultrasound system 100 may also show respiratoric cycles, muscle movements, cycles of antrum contractions, and the like. Furthermore, the image sequences need not be illustrative of biological systems. That is, the region of interest 108 may also include industrial mechanical or fluid systems that exhibit cyclic or non-cyclic behaviors.

Figure 2:
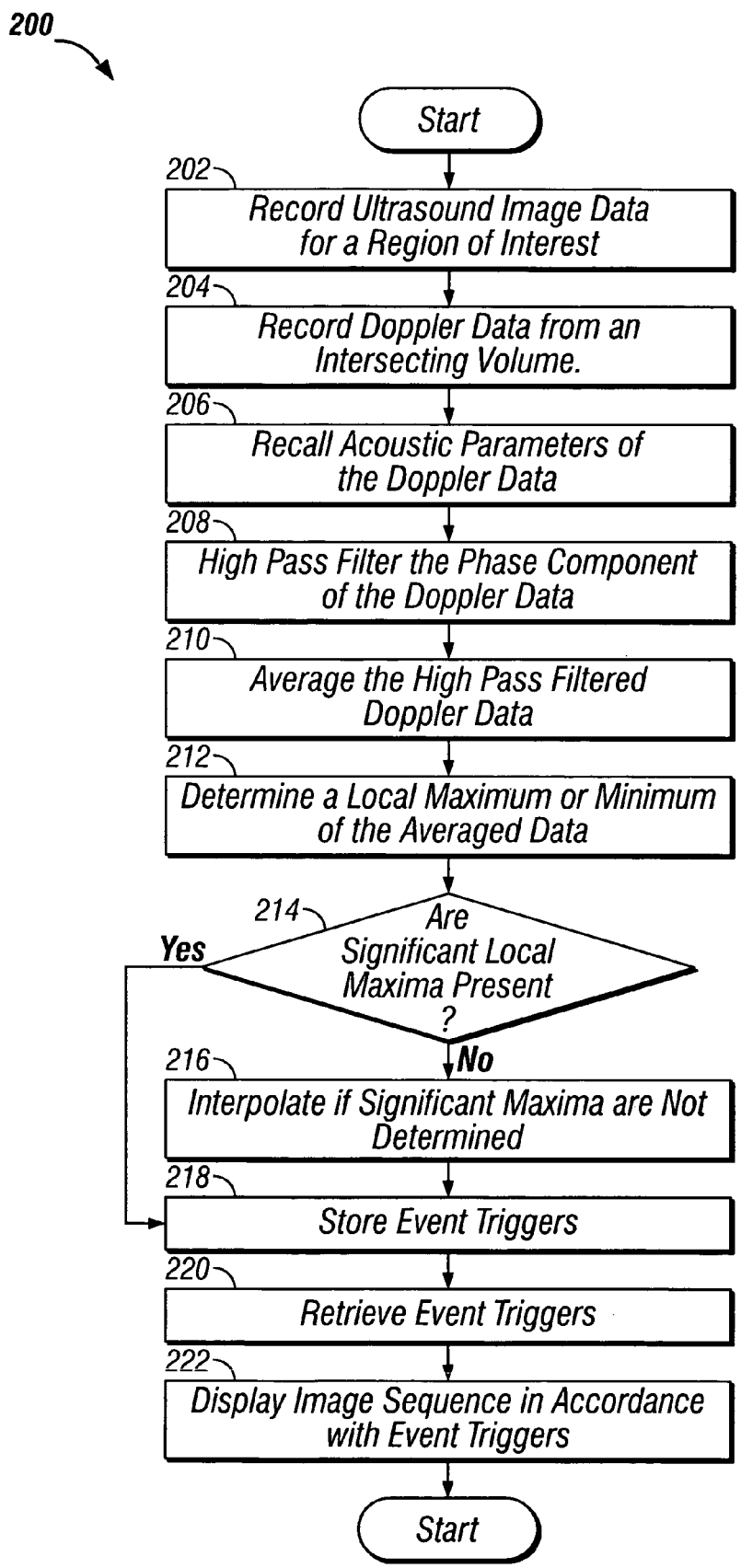
FIG. 2 shows a flow diagram of the operation of the ultrasound imaging system shown in FIG. 1.

FIG. 2 shows a flow diagram 200 of the steps taken by the ultrasound system 100, trigger extraction program 130, and image display program 140. Initially, the ultrasound system 100 records ultrasound image data for a region of interest (Step 202). The image data may be, as examples, color flow Doppler data, Tissue Velocity Doppler data, spectral Doppler data, and the like used to create B-mode scans over a selected angle (e.g., 25 degrees).

At the same time, the ultrasound system 100 records image data from a volume or slice intersecting the region of interest (Step 204) obtained by the same probe 104 or a different probe firing simultaneously (utilizing machine readable medium storing instructions). These image data are referred to as triggering data. The trigger data may be directly sampled ultrasound pulses or complex demodulated data obtained from one or more sample volumes and over one or more depth ranges from each sample volume. The volume intersecting the region of interest may be one beam (e.g., ranging from 1 to 10 degrees in both directions) or multiple beams. For example, 8 beams may be used to cover a whole B-mode sector.

Next, the ultrasound system 100 recalls the acoustic parameters of the triggering data (Step 206). The acoustic parameters include transmit and receive aperture, transmit and receive frequency, focus depth, time-gain compensation, and the like. The acoustic parameters are the parameters chosen when setting up the ultrasound scan.

Note that the acoustic parameters for the triggering data may be different than those for the image data for the region of interest. Furthermore, when the probe 104 uses an array of transducers 106 with dimensionality greater than 1 (such as a 1.5D, 1.75D or 2D array), the triggering data can optionally be recorded with a defocused beam (under control of the beamformer 114) in the azimuth direction, elevation direction, or both. Defocusing in the elevation direction takes into account the velocities of structures not present in the region of interest. Defocusing in the azimuth direction reduces the number of beams needed to cover a given area.

The trigger extraction program 130 analyzes the trigger data for a trigger characteristic. More specifically, the signal processor 120 may run the trigger extraction program 130 to analyze IQ data stored in the sample memory 118. The volume scan converter 132 and volume rendering processor 138 may use the IQ data and the resulting trigger characteristics as noted below. The trigger data analysis may include high pass filtering the trigger data to obtain filtered data (Step 208). In one embodiment, the filter is a digital regression filter that has a data dependent frequency cutoff. Because target motion is generally not in a fixed position, the trigger extraction program 130 may average the filtered data over all or some of the depth ranges and over all or some of the sample volumes (Step 210).

The trigger extraction program 130 subsequently searches for a pre-selected trigger characteristic in the trigger data (Step 212). For example, the trigger characteristic may be local minima and maxima in the trigger data. The maxima represents the greatest average velocity against the probe 104, while the minima represents the greatest velocity away from the probe 104. Other trigger characteristics may also be used, however.

More specifically, the event triggers may be obtained with an autocorrelation technique. The imaginary part of the autocorrelation function of lag 1 of Doppler I/Q samples forms a basis signal on which the trigger extraction program 130 applies a trigger selection function: s(t)=Im(mean(R1(r, theta, t))), where mean is taken over all or a portion of all (r, theta) in a frame. In other words, R1 is the imaginary part of the autocorrelation of lag 1 of the phase shift of the subsequent ultrasound pulses received at a specific depth at a specific steering angle. The trigger selection program 130 chooses as event triggers the time stamps of the local minima of s(t).

If no significant local minima or maxima are located (Step 214), then the trigger extraction program interpolates to obtain a trigger event (Step 216). The threshold for ascertaining whether a significant local minima or maxima exists may be pre-selected according to any desired criteria. In one embodiment, the threshold is set at 0.2 * max(-Im(mean (R1(r, theta, t)))), or 0.2 of the peak of the basis signal.

Similarly, many approaches may be taken to interpolating to find a trigger event. As one example, the trigger extraction program 130 may use: max(s(T−dt, T+dt)), where T is the equidistant time from a previous event trigger, and 2*dt is the length of the interval over which a new trigger event is sought. For fetal heart imaging, the seek interval may be approximately half of the cycle length and event triggers are obtained one per cycle (approximately 400 ms apart). Note, however, that the invention is not limited to any particular type of threshold selection or interpolation method. Furthermore, the threshold may vary over time, particularly if the trigger extraction techniques run in real time.

For heart cycles, note that although it is generally desirable to determine a trigger event for a specific event in each heart cycle, which particular event is not vital. However, it is generally desirable that the event is consistent from cycle to cycle. Thus, cyclic motions that can be split into single cycles which start on the same cyclic event are amenable to visualization with the techniques disclosed.

The trigger extraction program 130 stores the event triggers in memory for later retrieval (Step 218). Thus, the image display program 140 may retrieve the event triggers (Step 220) and prepare and display one or more image sequences synchronized by the event triggers (Step 222). For example, the image display program 140 may use the event triggers to synchronize the displayed images in the same manner that an ECG signal would be used in a clinical ultrasound to synchronize cineloop displays.

The image sequence may be a looping or non looping sequence of 1D, 2D, or 3D images, optionally using 3D volumes constructed from a B-mode sweep over the region of interest. Furthermore, the presentation format for the image sequence may take the form of a single or multiple loop display in which the ultrasound system 100 shows different recordings (from different examinations), each with multiple cineloops. The trigger events allow the ultrasound system 100 to show the recordings together, synchronized over the entire time span of the loops. That is, when one image sequence reaches a particular event as determined by a triggering event, the other image sequence is controlled to display that same event.

In addition, the image display program 140 may introduce a variable delay relative to a selected trigger event. Thus, for example, the display program 140 may present a single or loop of 2D images or 3D reconstructed volumes, which each volume reconstructed from imaging data obtained at an operator selected delay relative to the trigger event.

Figure 3:
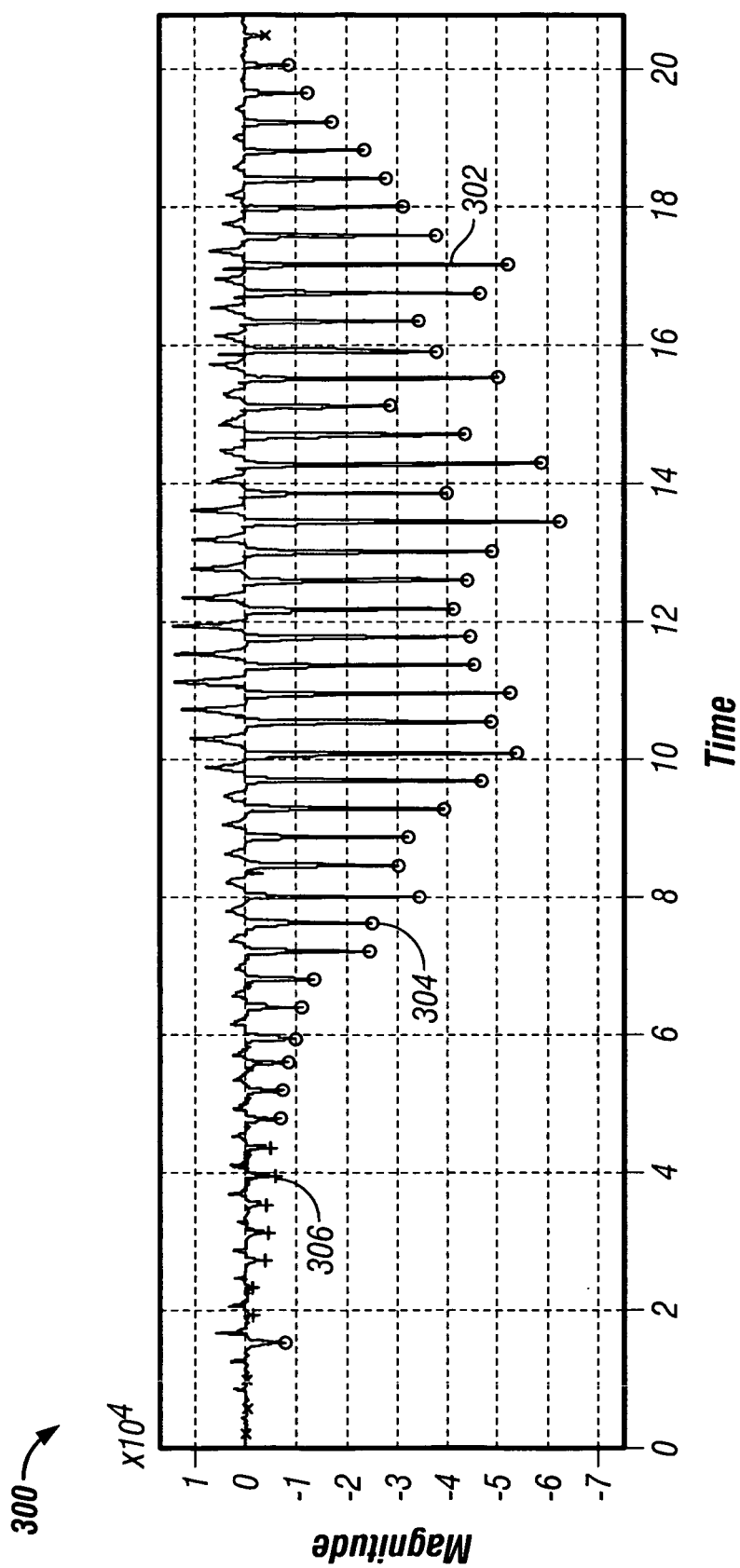
FIG. 3, that figure shows trigger events determined and interpolated from triggering data.

Turning briefly to FIG. 3, that figure shows an example of the triggering data 300 obtained during a fetal heart examination with a manual sweep of 25 degrees. More particularly, in FIG. 3, the solid line 302 shows the imaginary part of the spatial mean of the complex (I/Q) signal, the circles show the determined event triggers 304 (based on maxima/minima trigger characteristics), and the plus signs show the interpolated trigger events 306.

Figure 4:
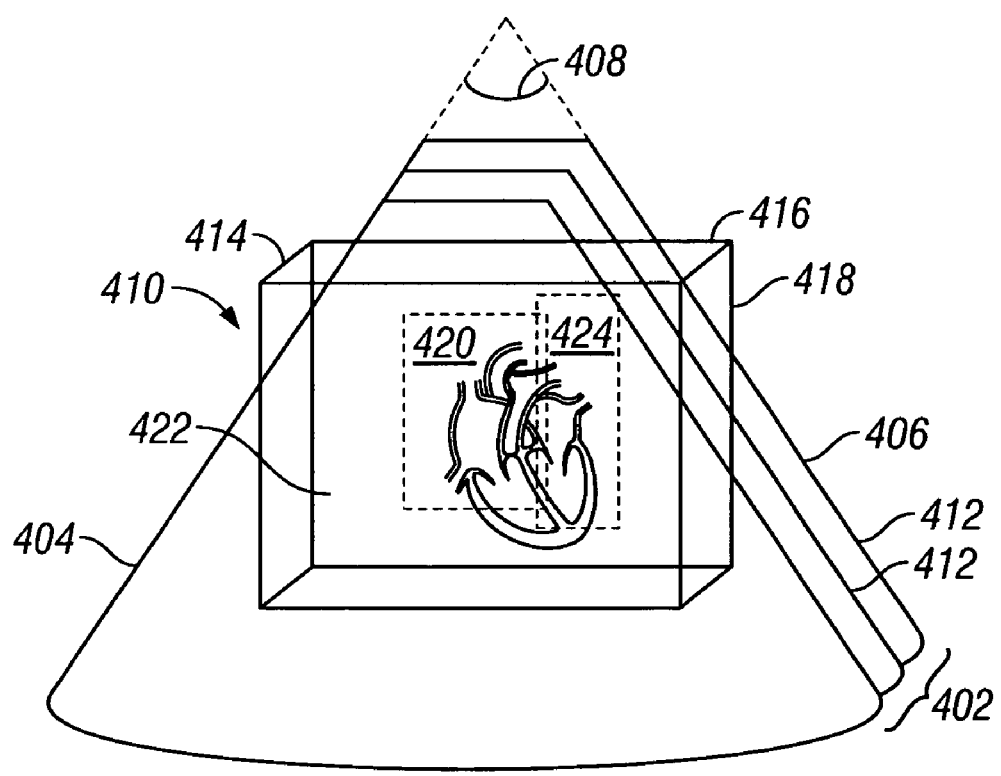
FIG. 4 shows a sample volume encompassing a region of interest and a triggering region influenced by the structures in the region of interest.

FIG. 4 illustrates a real-time 4D volume 402 acquired by the ultrasound system 100. The volume 402 includes a sector shaped cross-section with radial borders 404 and 406 diverging from one another at angle 408. The probe 104 and beamformer 114 electronically focus and direct ultrasound firings longitudinally to scan along adjacent scan lines in each scan plane 110 and electronically or mechanically focus and direct ultrasound firings laterally to scan adjacent scan planes 110. Scan planes 110 obtained by the probe 104 are stored in memory 118 and are scan converted from spherical to Cartesian coordinates by the volume scan converter 132. A volume comprising multiple scan planes is output form the volume scan converter 132 and stored in the slice memory 136 as the rendering box 410. The rendering box 410 in the slice memory 136 is formed from multiple adjacent image planes 412.

The rendering box 410 may be defined in size by an operator to have a slice thickness 414, width 416 and height 418. The volume scan converter 132 may be controlled by the slice thickness control input 134 to adjust the thickness parameter of the slice to form a rendering box 410 of the desired thickness. The rendering box 410 designates the portion of the scanned volume 402 that is volume rendered. The volume rendering processor 138 accesses the slice memory 136 and renders along the thickness 414 of the rendering box 410.

Predefined thicknesses for the rendering box 410 between 2 mm and 20 mm are typical, however, thicknesses less than 2 mm or greater than 20 mm may also be suitable depending on the application and the size of the area to be scanned. The slice thickness setting control 134 may include a rotatable knob with discrete or continuous thickness settings, a keyboard input, mouse input, or the like.

The volume rendering processor 138 projects the rendering box 410 onto an image portion 422 of an image plane 412. Following processing in the volume rendering processor 138, the pixel data in the image portion 422 may pass through the video processor 122 and then to a display 126. The rendering box 410 may be located at any position and oriented at any direction within the scanned volume 402. In some situations, depending on the size of the region being scanned, it may be advantageous for the rendering box 410 to be only a small portion of the scanned volume 402.

Still with reference to FIG. 3, a region of interest 420 is shown as a fetal heart. The ultrasound system 100 obtains triggering data from a trigger region 424. The trigger region need not be in the visible rendered image. Instead it may be an area out of view of the region of interest 420. The trigger region 424, however, is selected based on its ability to react to events that occur within the region of interest 420. Thus, muscle or tissue near the heart may make an appropriate trigger region because those tissues will react to the expansion and contraction of the heart. To that end, the trigger region may lie in a section or volume of image data intersecting the region of interest 420, or in an area disjoint from, but affected by events in the region of interest 420.

The event triggers correctly place images frames (e.g., B-mode frames) to one another in space and time. That is, the event triggers align the different heart cycles with one another when the event triggers are obtained in the same phases of each cycle. In other words, the ultrasound system 100 uses the event triggers to synchronize image display.

As one example of fetal heart imaging, the ultrasound system may use 1950 frames over 50 cardiac cycles with a frame rate of 96 (a time span of 20 seconds). The images may use 31 volumes, each assumed to have 50 equidistantly tilted frames. Each frame may have 91 beams with 583 samples each. The probe may be held, for example, 5 cm from the heart, which yields a radial resolution of 0.15 mm, azimuthal resolution of 0.3 degrees~0.26 mm and an elevational resolution of 0.5 degrees~0.44 mm.

The probe 104 may use a frequency range of 2-5 MHz, with second harmonic imaging giving high lateral resolution. The intra beam distance may be approximately 0.33 degrees. No particular distance is required, and other distances (e.g. 0.36, 0.51, and 0.55 degrees) may also be used. Increased frame rates result from increased intra beam distances.

While various embodiments of the invention have been described, it will be apparent to those of ordinary skill in the art that many more embodiments and implementations are possible that are within the scope of this invention.

What is claimed is:

1. A trigger extraction system for obtaining an event trigger for an event occurring in a region of interest while the region of interest is scanned by an ultrasound imaging system, the ultrasound imaging system having image memory and a display, the image memory storing image data defining a series of ultrasound images of a region of interest, the display displaying the ultrasound images, the trigger extraction system comprising:
   a processor;
   a memory coupled to the processor; and
   a trigger extraction program stored in the memory for execution by the processor, the trigger extraction program comprising instructions for accessing ultrasound trigger data obtained from a trigger region, analyzing the trigger data for a trigger characteristic, and storing an event trigger based on the trigger characteristic, the trigger data being recorded with an ultrasound beam defocused in an azimuth direction, the event trigger being used in connection with controlling display of the ultrasound images, wherein the instructions for analyzing comprise instructions for filtering the trigger data, the filter utilizing a cutoff frequency that is set based on the trigger characteristic independent of the image data.

2. The trigger extraction system of claim 1, where the trigger region at least partially differs from the region of interest.

3. The trigger extraction system of claim 1, wherein the trigger data comprises Doppler data with a phase component, and wherein the trigger extraction program further comprises instructions for high pass filtering the phase component based on the trigger characteristic.

4. The trigger extraction system of claim 1, where the instructions for analyzing the trigger data comprise instructions for averaging the trigger data over at least a portion of a depth range.

5. The trigger extraction system of claim 4, where the instructions for averaging the trigger data comprise instructions for averaging high pass filtered phase components of the trigger data.

6. The trigger extraction system of claim 4, wherein the instructions for analyzing the trigger data further comprise instructions for interpolating an additional event trigger.

7. The trigger extraction system of claim 1, where the trigger data and image data are recorded using ultrasound beams having different values for at least one acoustic parameter.

8. The trigger extraction system of claim 1, wherein the instructions for analyzing comprise instructions for determining at least one of a signal maxima and signal minima.

9. The trigger extraction system of claim 1, wherein the region of interest is a fetal heart.

10. The trigger extraction system of claim 9, wherein the trigger region comprises fetal tissue.

11. A machine readable medium storing instructions that cause an ultrasound imaging system that obtains images of a region of interest to perform a method, the ultrasound imaging system having image memory and a display, the image memory storing image data defining a series of ultrasound images of a region of interest, the display displaying the ultrasound images, the method comprising:
   accessing ultrasound trigger data obtained from a trigger region, the trigger data being recorded with an ultrasound beam defocused in an azimuth direction;
   analyzing the trigger data for a trigger characteristic; and
   storing an event trigger based on the trigger characteristic, the event trigger being used in connection with controlling display of the ultrasound images, where the trigger data comprises Doppler data, and wherein the step of analyzing comprises high pass filtering the Doppler data utilizing a cutoff frequency that is set based on the trigger characteristic independent of the image data.

12. The machine readable medium of claim 11, wherein the trigger region at least partially differs from the region of interest.

13. The machine readable medium of claim 11, wherein the step of analyzing comprises the step of averaging a high pass filtered component of the trigger data.

14. The machine readable medium of claim 11, wherein the trigger data and image data are recorded using ultrasound beams having different values for at least one acoustic parameter.

15. The machine readable medium of claim 11, where the step of analyzing comprises the step of determining a signal extreme from the trigger data.

16. The machine readable medium of claim 11, wherein the step of analyzing comprises the steps of determining high pass filtered trigger data, and determining at least one of a signal maxima and signal minima of the high pass filtered trigger data.

17. The machine readable medium of claim 11, wherein the region of interest is a fetal heart.

18. The machine readable medium of claim 17, wherein the trigger region comprises fetal tissue.

19. A method for obtaining an event trigger for an event occurring in a region of interest utilizing an ultrasound imaging system, the ultrasound imaging system having image memory and a display, the image memory storing image data defining a series of ultrasound images of a region of interest, the display displaying the ultrasound images, the method comprising:

accessing ultrasound trigger data from a trigger region, the trigger data being recorded with an ultrasound beam defocused in an azimuth direction;

analyzing the trigger data for a trigger characteristic; and storing an event trigger based on the trigger characteristic, the event trigger being used in connection with controlling display of the ultrasound images, wherein the trigger data comprises Doppler data, and wherein the analyzing comprises high pass filtering the Doppler data utilizing a cutoff frequency that is set based on the trigger characteristic independent of the image data.

20. The method of claim 19, wherein the step of analyzing comprises the step of averaging the trigger data in a depth range.

21. The method of claim 19, wherein the step of analyzing comprises the step of averaging a high pass filtered component of the trigger data.

22. The method of claim 19, wherein the step of analyzing comprises the step of interpolating an additional event trigger.

23. The method of claim 19, where the step of analyzing comprises the step of determining a signal extreme from the trigger data.

24. The method of claim 19, wherein the step of analyzing comprises the steps of determining high pass filtered trigger data, and determining at least one of a signal maxima and signal minima of the high pass filtered trigger data.

25. The method of claim 19, wherein the region of interest is a fetal heart.

26. The method of claim 25, wherein the trigger region comprises fetal tissue.

27. An ultrasound imaging system comprising:

an ultrasound probe for obtaining ultrasound trigger data from a trigger region intersecting a region of interest, the ultrasound imaging system having image memory and a display, the image memory storing image data defining a series of ultrasound images of a region of interest, the display displaying the ultrasound images;

a processor;

a memory coupled to the processor;

a trigger extraction program stored in the memory for execution by the processor, the trigger extraction program comprising instructions for accessing the ultrasound trigger data, analyzing the trigger data for a trigger characteristic, and storing an event trigger based on the trigger characteristic, the trigger data being recorded with an ultrasound beam defocused in an azimuth direction, wherein the trigger data comprises Doppler trigger data compromising a phase component, and wherein the instructions for analyzing the trigger data comprise instructions for high pass filtering the phase component to obtain filtered data, averaging the filtered data to obtain averaged data, determining a signal extreme of the averaged data to determine the event trigger;

an image display program stored in the memory for execution by the processor, the image display program comprising instructions for accessing the event trigger and for displaying at least one image in a sequence of images in synchronism with the event trigger; and a display for displaying the sequence of images.

28. The ultrasound imaging system of claim 27, further comprising a beamformer that defocuses the ultrasound beam in the azimuth direction and in an elevation direction.

29. The ultrasound imaging system of claim 27, wherein the region of interest is a fetal heart.

30. The ultrasound imaging system of claim 27, wherein the trigger region comprises fetal tissue.

31. The ultrasound imaging system of claim 27, further comprising the step of interpolating to obtain the event trigger.

32. The ultrasound imaging system of claim 27, wherein the instructions for analyzing the trigger data comprise instructions for determining a signal extreme from signal values determined by:

$s(t)=Im(mean(R1(r, theta, t)))$, where $Im(\ )$ represents an imaginary part of $mean(R1(r, theta, t))$, $R1$ is an imaginary part of autocorrelation of lag one, r represents depth, theta represents a steering angle, and t represents time.

* * * * *